US011185598B2

(12) United States Patent
Glogard et al.

(10) Patent No.: US 11,185,598 B2
(45) Date of Patent: Nov. 30, 2021

(54) PREPARATION OF STABILISED X-RAY DIAGNOSTIC COMPOSITION

(75) Inventors: Christian Glogard, Oslo (NO); Dirk-Jan in't Veld, Oslo (NO)

(73) Assignee: GE HEALTHCARE AS, Oslo (NO)

( * ) Notice: Subject to any disclaimer, the term of this patent is extended or adjusted under 35 U.S.C. 154(b) by 1658 days.

(21) Appl. No.: 13/582,790

(22) PCT Filed: Mar. 22, 2011

(86) PCT No.: PCT/EP2011/054341
§ 371 (c)(1),
(2), (4) Date: Sep. 5, 2012

(87) PCT Pub. No.: WO2011/117236
PCT Pub. Date: Sep. 29, 2011

(65) Prior Publication Data
US 2013/0004433 A1 Jan. 3, 2013

(30) Foreign Application Priority Data
Mar. 23, 2010 (EP) .................. 10157336

(51) Int. Cl.
*A61K 49/04* (2006.01)

(52) U.S. Cl.
CPC ...... *A61K 49/0433* (2013.01); *A61K 49/0452* (2013.01)

(58) Field of Classification Search
CPC .............. A61K 49/0433; A61K 49/0452
See application file for complete search history.

(56) References Cited

U.S. PATENT DOCUMENTS

| | | | |
|---|---|---|---|
| 4,278,654 | A | 7/1981 | Rakli et al. |
| 4,396,597 | A | 8/1983 | Rakli et al. |
| 4,863,714 | A | 9/1989 | Sovak et al. |
| 5,204,086 | A | 4/1993 | Knut |
| 2005/0025711 | A1 | 2/2005 | Sovak et al. |
| 2005/0084453 | A1 | 4/2005 | Eiichi et al. |
| 2008/0317675 | A1 | 12/2008 | Periasamy et al. |
| 2009/0005595 | A1 | 1/2009 | Janssen et al. |
| 2010/0322868 | A1 | 12/2010 | Thaning |

FOREIGN PATENT DOCUMENTS

| | | |
|---|---|---|
| CN | 1738651 | 2/2006 |
| CN | 1738651 A | 2/2006 |
| CN | 1938050 A | 3/2007 |
| CN | 101687051 A | 3/2010 |
| EP | 0278674 A2 | 8/1988 |
| EP | 877628 A2 | 11/1998 |
| EP | 1009445 A2 | 6/2000 |
| EP | 1575621 A2 | 9/2005 |
| EP | 1679084 A1 | 7/2006 |
| EP | 1725268 A2 | 11/2006 |
| EP | 1901783 B1 | 3/2008 |
| EP | 2178568 B1 | 4/2010 |
| GB | 2465663 * | 2/2010 ............ A61K 49/04 |
| JP | S5531068 S | 3/1980 |
| JP | 01-221330 H | 9/1989 |
| JP | 2000-504334 A | 4/2000 |
| JP | 2001-504837 A | 4/2001 |
| JP | 2005-170923 A | 6/2005 |
| JP | 2006-509841 A | 3/2006 |
| JP | 2007-528424 A | 10/2007 |
| JP | 2009-500441 A | 1/2009 |
| JP | 2010-533172 A | 10/2010 |
| KR | 10-2005-0088312 A | 9/2005 |
| KR | 10-2007-0015517 A | 2/2007 |
| KR | 10-2014-0111350 A | 9/2014 |
| WO | 1997/28104 A2 | 8/1997 |
| WO | 98/23297 | 6/1998 |
| WO | 1998/023297 A2 | 6/1998 |
| WO | 00/26179 | 5/2000 |
| WO | 2004/054637 A2 | 7/2004 |
| WO | 2005/037325 A1 | 4/2005 |
| WO | 2005/087272 | 9/2005 |
| WO | 2005/087272 A2 | 9/2005 |
| WO | 2007/007021 | 1/2007 |
| WO | 2007/007021 A | 1/2007 |
| WO | 2009/008734 | 1/2009 |
| WO | 2009/008734 A2 | 1/2009 |

OTHER PUBLICATIONS

Davies et al., Letters in Applied Microbiology, 1998, 27, p. 186-187. (Year: 1998).*
Amersham Health (Visipaque, May 2003, https://www.accessdata.fda.gov/drugsatfda_docs/label/2003/20808slr004_visipaque_lbl.pdf (Year: 2003).*
Marraccini et al., Acta Radiologica, 2013, 54, p. 42-47 (Year: 2013).*
Preibe et al., J. of Clin. Pharm. and Ther., 1999, 24, p. 227-235. (Year: 1999).*
PCT/EP2011/054341 ISRWO dated Jul. 20, 2011.
Chinese Office Action regarding Chinese Application No. 2013-500468, dated Mar. 31, 2015, 3 pages.
English language translation of Chinese Office Action regarding Chinese Application No. 2013-500468, dated Mar. 31, 2015, 5 pages.

(Continued)

*Primary Examiner* — Michael G. Hartley
*Assistant Examiner* — Leah H Schlientz
(74) *Attorney, Agent, or Firm* — Jeff B. Vockrodt; Culhane Meadows, PLLC

(57) ABSTRACT

The invention relates to a process for the preparation of a diagnostic X-ray composition. The composition comprises a non-ionic X-ray contrast agent in a pharmaceutically acceptable carrier. More particularly, the invention relates to a process for secondary production of X-ray compositions comprising X-ray contrast agents with a high dissolution temperature. When using the process of the invention, precipitation is avoided and degradation of the contrast agent is reduced. The process of the invention includes heat treatment of iodinated X-ray contrast agents at low pH.

13 Claims, 2 Drawing Sheets

(56) References Cited

OTHER PUBLICATIONS

English translation of Chinese Office Action regarding Chinese Application No. 201180015249.4, dated May 9, 2013, 12 pages.
European Search Report from EP Appl. No. 88 30 0926, dated Apr. 21, 1989.
European Office Action for EP Patent Appl. No. 11 709 146.2, filed Mar. 22, 2011, 5 pages, dated Jan. 11, 2017.
Notice of Preliminary Rejection Received for Korean Patent Application No. 10-2012-7024712 dated Dec. 15, 2017, 16 Pages (7 pages Official Copy + 9 Pages English Translation).

* cited by examiner

Figure 1. Iodide levels and end pH as a result of start pH and a heat load of 121 °C for 120 minutes, composition of Compound I.
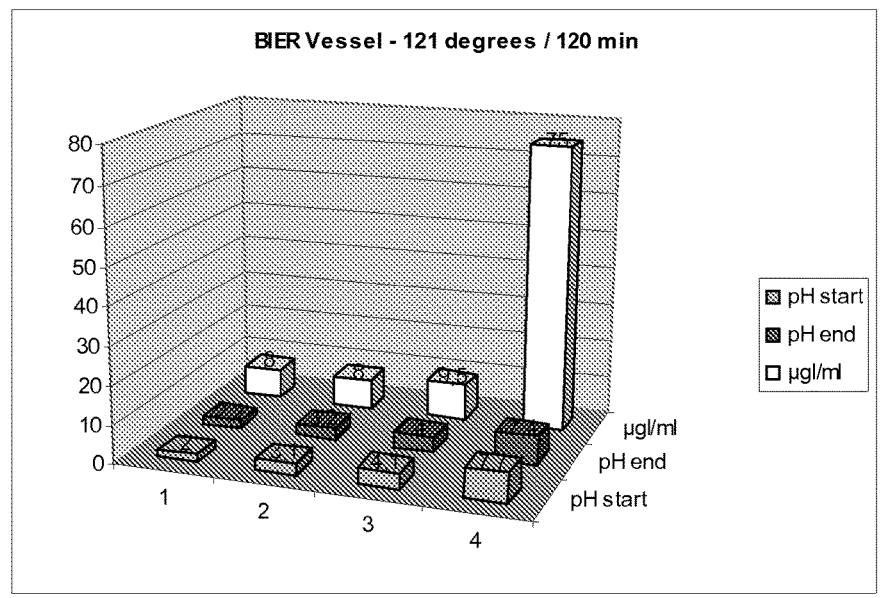
Figure 2. Iodide levels and end pH as a result of start pH and a heat load of 134 °C for 60 minutes, composition of Compound I.
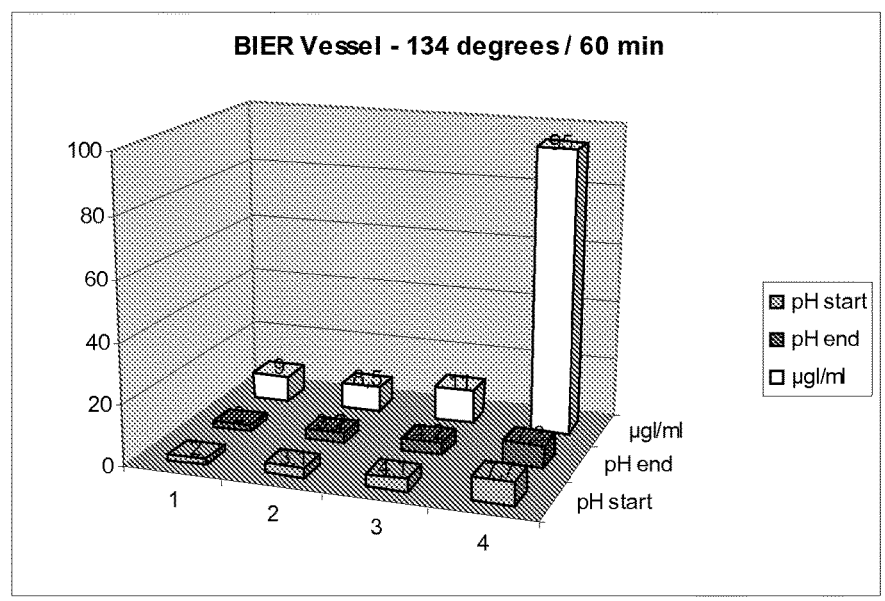

Figure 3: Production set up for the process of the invention.
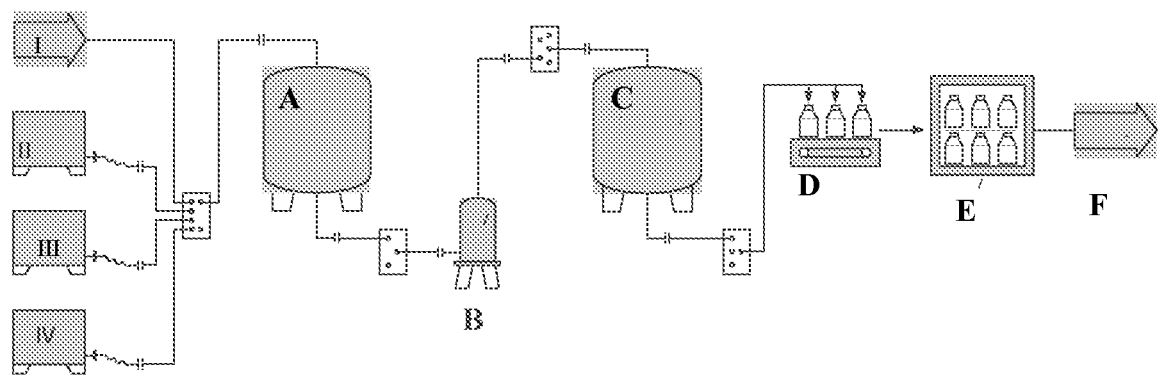

PREPARATION OF STABILISED X-RAY DIAGNOSTIC COMPOSITION

This application is a filing under 35 U.S.C. 371 of international application number PCT/EP2011/054341, filed Mar. 22, 2011, which claims priority to EP application number 10157336.8 filed Mar. 23, 2010, the entire disclosure of each of which is hereby incorporated by reference.

The present invention relates to a process for the preparation of a diagnostic X-ray composition. The composition comprises a non-ionic X-ray contrast agent in a pharmaceutically acceptable carrier. More particularly, the invention relates to a process for secondary production of supersaturated X-ray compositions comprising X-ray contrast agents with a high dissolution temperature in water. When using the process of the invention, degradation of the contrast agent during dissolution through heating is avoided. Consequently, degradation, and precipitation due to incomplete dissolution, is prevented.

All diagnostic imaging is based on the achievement of different signal levels from different structures within the body. Thus, in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution. The diagnostic quality of images is strongly dependent on the inherent noise level in the imaging procedure, and the ratio of the contrast level to the noise level can thus be seen to represent an effective diagnostic quality factor for diagnostic images. Achieving improvement in such a diagnostic quality factor has long been and still remains an important goal.

In techniques such as X-ray, one approach to improve the diagnostic quality factor has been to introduce contrast enhancing materials formulated as contrast media into the body region being imaged. Thus for X-ray, early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media containing iodinated contrast agents are usually classified as ionic monomers such as diatrizoate (marketed e.g. under the trade mark Gastrografen™), ionic dimers such as ioxaglate (marketed e.g. under the trade mark Hexabrix™), nonionic monomers such as iohexyl (marketed e.g. under the trade mark Omnipaque™), iopamidol (marketed e.g. under the trade mark Isovue™), iomeprol (marketed e.g. under the trade mark Iomeron™) and the non-ionic dimer iodixanol (marketed under the trade mark Visipaque™). The clinical safety of iodinated X-ray contrast media has continuously been improved over the recent decades through development of new agents; from ionic monomers (Isopaque™) to non-ionic monomers (e.g. Omnipaque™) and non-ionic dimers (e.g. Visipaque™).

The utility of the contrast media is governed largely by its toxicity, by its diagnostic efficacy, by adverse effects it may have on the subject to which the contrast medium is administered, but also by the ease of production, storage and administration. The toxicity and adverse biological effects of a contrast medium are contributed to by the components of the formulation medium, i.e. of the diagnostic composition, e.g. the solvent or carrier as well as the contrast agent itself and its components such as ions for the ionic contrast agents and also by its metabolites.

The manufacture of non-ionic X-ray contrast media involves the production of the chemical drug, the active pharmaceutical ingredient (API), i.e. the contrast agent (referred to as the primary production), followed by the formulation into the drug product (referred to as the secondary production), herein denoted the X-ray composition. In the preparation of an X-ray composition, i.e. the secondary production of a contrast media, the contrast agent is admixed with additives, such as salts, optionally after dispersion in a physiologically tolerable carrier. The contrast agent, such as a non-ionic iodinated compound, e.g. a non-ionic monomer or non-ionic dimer, has to be completely solved in the carrier when additives are included and the composition is prepared. A well-known process for preparing X-ray compositions includes heating the contrast agent in the carrier, such as water for injection, to ensure complete dissolution. For instance for the contrast media Visipaque™ the secondary production process includes dissolution of the contrast agent iodixanol in water for injection and heating to about 98° C. Heating at this temperature for an adequate period of time ensures that the contrast agent is completely dissolved.

However, different X-ray contrast agents have different solubility resulting in different challenges in the secondary production. For instance WO 2009/008734 of GE Healthcare AS discloses a new class of compounds and their use as X-ray contrast agents. The compounds are dimers containing two linked iodinated phenyl groups. The bridge linking the two iodinated phenyl groups is a straight $C_3$ to $C_8$ alkylene chain optionally substituted by one to six —OH or —OCH$_3$ groups. Compound I, which is one specific dimeric X-ray contrast agent, falling within the formula I of WO2009/008734, has been found by the applicant to have favourable properties:

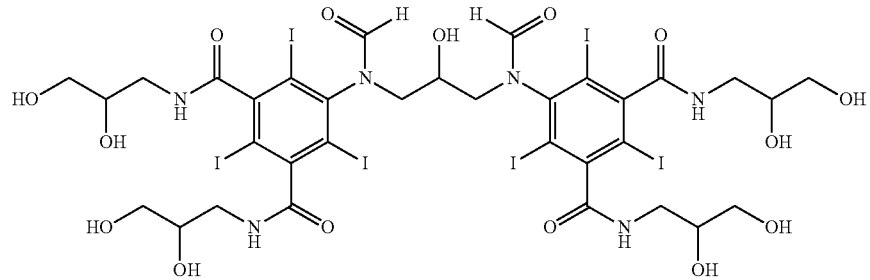 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound I: 5-[formyl-[3-[formyl-[3,5-bis(2,3-dihydroxypropylcarbamoyl)-2,4,6-triiodophenyl]amino]-2-hydroxypropyl]amino]-N,N'-bis(2,3-dihydroxypropyl)-2,4,6-triiodobenzene-1,3-dicarboxamide.

The injection solution of Compound I is highly supersaturated. The nucleation (precipitation) in the injection solution at storage conditions is strongly undesirable. The physical stability of the solution, i.e. prevention of the nucleation for a certain time at storage conditions, may be improved substantially by heat treatment of the solution well above its saturation temperature for a sufficiently long period of time. A solution in which the concentration of the solute (API) exceeds the equilibrium solute concentration at a given temperature is said to be supersaturated. This is possible because the solute does not precipitate immediately when the solution is cooled below the saturation temperature. Such solutions are denoted as supersaturated. Saturation temperature is the temperature where all solid API (amorphous and crystalline) apparently dissolves completely. As the solubility of Compound I decreases with decreasing temperature, the supersaturation increases.

Supersaturated solutions are thermodynamically unstable, are prone to nucleate and therefore precipitate on storage. However, the onset of precipitation (nucleation) may be delayed by a proper treatment of the solution. The onset of the precipitation depends mainly on the degree of supersaturation, presence of the crystals of the solute and foreign particles such as dust or other impurities, i.e. purity, and storage temperature of the solution.

Compound I has a lower solubility in water than iodixanol and a higher dissolution temperature in water. Typically, for a solution of about 320 mg I/ml in water, a solution of iodixanol is saturated at approximately 92° C., whereas a similar solution of compound I is saturated at approximately 110° C. Establishing the parameters for the secondary production of compound I have therefore been challenging. Compared to iodixanol, a higher heat load would be necessary during the processing to ensure complete dissolution of crystalline material present in the largely amorphous bulk X-ray contrast medium. When exposing the composition to this higher heat load while keeping other parameters the same, high levels of free iodide and a lower pH than wanted are however obtained in the final product. Hence, increasing the temperature to ensure dissolution causes greater degradation in the composition. To avoid such problem, one possible solution could be to restrict the heating regime as much as possible. However, a restricted heat regime would put the physical stability of the product at risk due to incomplete dissolution of the X-ray contrast agent, i.e. there is a risk of precipitation of crystalline material when the composition after heating is kept at temperatures below the dissolution temperature and hence becomes supersaturated. Therefore, a process for preparation of X-ray compositions has been sought which during the process implicates extensive heating of an aqueous solution of an X-ray contrast agent, resulting in complete dissolution and an acceptably low level of degradation.

During the development of new iodinated X-ray contrast agents, several heating regimes have been tested to find the parameters to be used for the secondary productions. Among these are end heat steam sterilization at 134° C. or 121° C. for 45 minutes or more, pre-heating in the mixing tank above the dissolution temperature (e.g. 110-111° C./330 mg I/ml) using different regimes followed by end heat steam sterilization etc. Although some of these heating regimes might be capable of providing a physically stable solution, they may cause high levels of free iodide due to degeneration of the iodinated X-ray contrast agent (Scheme 1). For Compound I it was found that typical iodide levels after steam heat sterilisation at 134° C. for 45 minutes were 75-85 µg I/ml. This is above the acceptable level.

Scheme 1. Cleavage of iodide from Compound I.

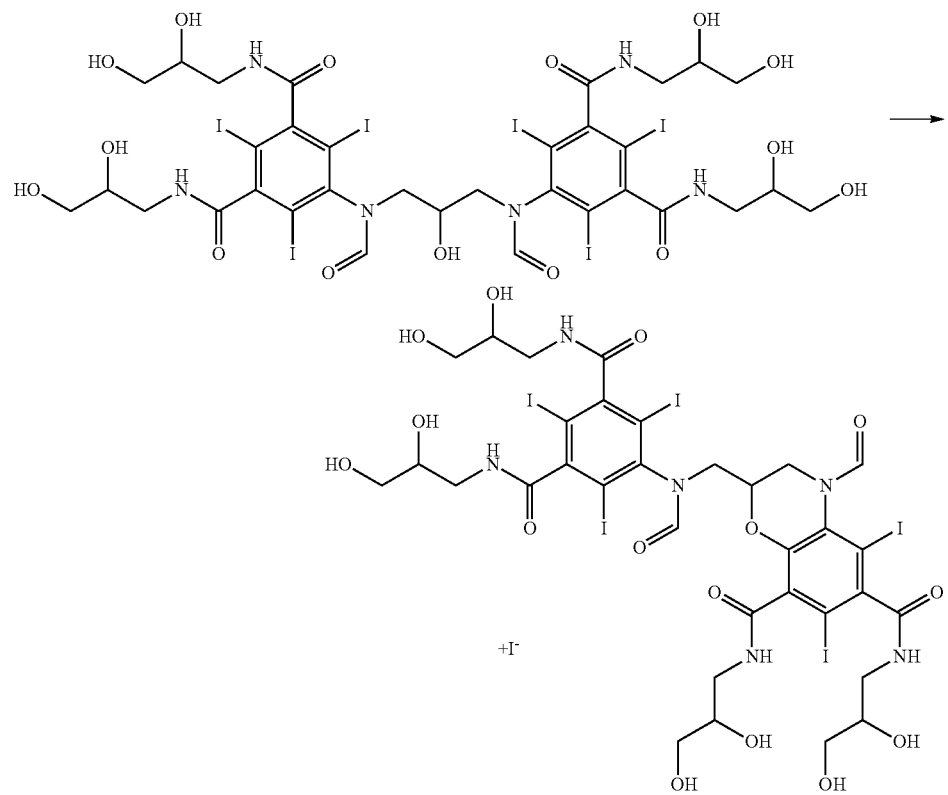

In the process of Scheme 1 H⁺ is also generated, hence such degradation results in both free iodide generation and a reduced pH.

To provide a process for the preparation of an X-ray contrast composition, completely dissolving the comprising X-ray contrast agent, and avoiding degradation, experiments were performed to investigate the level of inorganic iodide as a factor of pH and heating regime. It was surprisingly found that by applying the majority of the heat load at significantly reduced pH the contrast agent is completely dissolved in the carrier, it is maintained stable and the amount of free iodide in the composition is well below the acceptable level. This was confirmed by production of a 400 litre scale X-ray composition batch of compound I using the process of the invention.

Thus, in a first aspect the invention provides a process for the preparation of an X-ray composition comprising an X-ray contrast agent in a carrier, the process comprising the steps of i) adjusting the pH of the carrier comprising the X-ray contrast agent to 2.0-4.5;
ii) heating the pH-adjusted composition of step i) to 60-200° C.;
iii) cooling the composition of step ii) to 40-60° C.;
iv) adjusting the pH of the heated composition of step iii) to 7.0-8.0.

The steps i) to iv) are preferably carried out in sequential order as provided, with optional additional steps as later described.

Hence, heat treatment of iodinated X-ray contrast agents at low pH has been found to be a key solution to the problems of secondary production directed to precipitation of the contrast agent and degeneration of this resulting in free iodide in the composition. It has been found that by using the process of the invention the amount of free iodide in the prepared diagnostic X-ray composition is below 30 µgI/ml, or more preferably below 25 µgI/ml, or even more preferably below 20 µgI/ml.

In step i) the pH of the carrier comprising the X-ray contrast agent is adjusted to 2.0-4.5 and more preferably to 3.0-4.0. It has surprisingly been found that contrast agents not soluble by solely heating a carrier comprising such, can be completely dissolved by adjusting the pH as specified. Further, the contrast agents, such as compound I, have been found to be stable enough to undergo heating well above the dissolution temperature (e.g. 110-111° C. at 330 mg I/ml for compound I) for as long as it takes to achieve complete dissolution without causing the amount of free iodide to rise significantly. The pH in step i) is adjusted by adding an acid to the composition comprising a contrast agent and a carrier. The acid is preferably selected from the group of hydrochlorid acid (HCl) and phosphoric acid ($H_3PO_4$), HCl being preferred. The concentration of the contrast agent in the carrier at this stage of the process is e.g. 270-400 mg I/ml, such as 320-380 mg I/ml or more preferably 330-360 mg I/ml. The concentration can become reduced, or can be adjusted, in the following steps of the process.

In step ii) the pH-adjusted composition from step i) is heated to ensure complete dissolution of the contrast agent. To increase the physical stability of the solution, i.e. prevent precipitation for a certain period of time, the solution should be heated to a temperature above the saturation temperature of the solution for an appropriate period of time. The temperature needed will vary for different contrast agents and will typically be 60-200° C., more preferably 90-135° C. and most preferably 110-135° C. and even more preferably around 120° C. For a composition of compound I with a concentration of 320 mg I/ml the saturation temperature is about 110° C., and appropriate heating temperature for this solution may be 120° C. There are different ways of heating the pH adjusted composition, such as in a continuously stirred mixing tank, through a heat exchanger, or in a continuous tube reactor, and a preferred option is a continuously stirred mixing tank. The pH adjusted composition is heated at a temperature, and for a period, needed to completely dissolve the contrast agent. An appropriate period of time is 10-240 minutes, more preferably 10-120 minutes, preferably 10-60 minutes, and most preferably 30-40 minutes.

In step iii) the composition from step ii) is cooled to 40-60° C., more preferably 45-55° C. The cooling is done e.g. by changing the jacked temperature or, turning heat off and allowing the solution to obtain the desired temperature. In one embodiment a rapid cooling, particularly to below the saturation temperature, is performed, as this can have a positive effect on the physical stability of the solution.

In step iv) the pH of the composition from step iii) is adjusted to 7.0 to 8.0 and more preferably to 7.2-7.8 and most preferably to 7.4-7.7. The pH is adjusted by adding an appropriate buffer, such as the buffer couple TRIS/TRIS HCl (TRIS denoting tris(hydroxymethyl)aminomethane). TRIS has a pKa of 8.06, which implies that the buffer has an effective pH range between 7.0 and 9.2, and its pKa declines with rising temperature. Other buffers with similar properties may also be considered, e.g. a phosphate buffer ($KH_2PO_4/Na_2HPO_4$) should be used if phosphoric acid is used in the pH adjustment of step i). Other relevant buffers are ACES, PIPES, imidazoles, /HCl, BES, MOPS, HEPES, TES, HEPPS OR TRICIN. Accordingly, the pH is adjusted in step iv) by the addition of a buffer selected from the group of TRIS/TRIS HCl, $KH_2PO_4/Na_2HPO_4$, ACES (N-(2-Acetamido)-2-aminoethanesulfonic acid), PIPES (piperazine-N, N'-bis(2-ethanesulfonic acid)), imidazoles, /HCl, BES (N,N-Bis(2-hydroxyethyl)-2-aminoethanesulfonic Acid), MOPS (3-(N-morpholino)propanesulfonic acid), HEPES (4-2-hydroxyethyl-1-piperazineethanesulfonic acid), TES (N-Tris(hydroxymethyl)methyl-2-aminoethanesulfonic Acid), HEPPS (3-[4-(2-hydroxyethyl)piperazin-1-yl]propane-1-sulfonic acid) and TRICIN(N-(2-Hydroxy-1,1-bis(hydroxymethyl)ethyl)glycine), and is most preferably TRIS/TRIS HCl.

The process of the invention is useful for secondary production of supersaturated X-ray compositions comprising X-ray contrast agents with a high dissolution temperature in water. Hence, the process may be used for contrast agents that have a low solubility or preparation of a concentrated composition.

For a compound or contrast agent with a defined crystalline state (single polymorph) at one side, and a solvent including dissolved admixtures on the other, the concentration of the agent in the solution in equilibrium with the crystalline state is called solubility. At this concentration the activity of the agent is equal in both phases. A system out of the equilibrium stage tends to change the solution concentration towards the equilibrium (solubility), e.g. dissolve crystals when under-saturated, or crystallize out compound when supersaturated. Normally, the solubility changes, usually increases, with temperature. For the purpose, we define the temperature at which the crystal solubility is equal to the concentration in the particular solution as "dissolution temperature". When a solution contains crystals, the crystals dissolve at temperatures above the "dissolution temperature", remaining a crystal free solution. When the amount of the crystals is small, the concentration increase by dissolution may be neglected.

In the case of secondary production of Compound I, using water for injection as the solvent, the dissolution temperature within the concentration range of e.g. 270-380 mg I/ml will differ only a few degrees from 110° C.

The X-ray contrast agents used in the aqueous composition prepared by the process of the invention may be any iodinated X-ray contrast agents that require heat to be solved. Iodinated compounds are well known and widely used as X-ray contrast agents, in particular compounds based on one or more triiodinated aryl groups, such as monomers, dimers and trimers. A number of such chemical compounds are known such as diatrizoat, ioxaglate, iopamidol, iomeprol, iodixanol, iohexyl, iopentol, ioversol, iopromide, iosimide, metrizamide, iotasol and iotrolan. Chemical compounds containing one or two triiodinated aryl groups, i.e. monomers and dimers, in particular aryl groups with iodine atoms in the 1,3 and 5 positions on a benzene ring and further being substituted in the remaining positions with non-ionic substitiuents, are preferred. These compounds form the class of compounds denoted non-ionic iodinated X-ray contrast compounds or agents, of which the compounds iopamidol, iomeprol, iodixanol, iohexyl, ioversol, iopromide and the compound of formula I are particularly preferred.

In one embodiment of the invention, the contrast agent used in the process of preparation is a non-ionic iodinated compound being either a non-ionic iodinated monomeric compound or a non-ionic iodinated dimeric compound. The contrast agent being a monomeric compound includes compounds of the general formula (I)

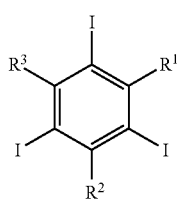

Formula (I)

or optical active isomers thereof,
wherein each of $R^1$, $R^2$ and $R^3$ are the same or different and denotes a hydrogen atom or a non-ionic hydrophilic moiety, provided that at least one of the $R^1$, $R^2$ and $R^3$ groups in the compound of formula (I) is a hydrophilic moiety.

In formula (I) above, the non-ionic hydrophilic moieties $R^1$, $R^2$ and $R^3$ may be any of the non-ionizing groups conventionally used to enhance water solubility. Hence, the $R^1$, $R^2$ and $R^3$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or $CH$ moieties replaced by oxygen or nitrogen atoms. The $R^1$, $R^2$ and $R^3$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred embodiment, the $R^1$, $R^2$ and $R^3$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via amide and/or carbamoyl linkages.

The $R^1$, $R^2$ and $R^3$ groups of the formulas listed below are particularly preferred:

—$CONH_2$
—$CONHCH_3$
—$CONH—CH_2—CH_2—OH$
$CONH—CH_2—CH_2—OCH_3$
—$CONH—CH_2—CHOH—CH_2—OH$
—$CONH—CH_2—CHOCH_3—CH_2—OH$
—$CONH—CH_2—CHOH—CH_2—OCH_3$
—$CON(CH_3)CH_2—CHOH—CH_2OH$
—$CONH—CH—(CH_2—OH)_2$
—$CON—(CH_2—CH_2—OH)_2$
—$CON—(CH_2—CHOH—CH_2—OH)_2$
—$CONH—OCH_3$
—$CON(CH_2—CHOH—CH_2—OH)(CH_2—CH_2—OH)$
—$CONH—C(CH_2—OH)_2 CH_3$
—$CONH—C(CH_2—OH)_3$ and
—$CONH—CH(CH_2—OH)(CHOH—CH_2—OH)$
—$NH(COCH_3)$
—$N(COCH_3)$ $C_{1-3}$ alkyl
—$N(COCH_3)$—mono, bis or tris-hydroxy $C_{1-4}$ alkyl
—$N(COCH_2OH)$—hydrogen, $C_{1-4}$ alkyl, mono, bis or tris-hydroxy $C_{1-4}$ alkyl
—$N(CO—CHOH—CH_2OH)$— hydrogen, mono, bis or tri-hydroxylated $C_{1-4}$ alkyl
—$N(CO—CHOH—CHOH—CH_2OH)$— hydrogen, mono, bis or trihydroxylated $C_{1-4}$ alkyl
—$N(CO—CH—(CH_2OH)_2)$—hydrogen, mono, bis or tri-hydroxylated $C_{1-4}$ alkyl
—$N(CO—CHOH—CH_3)$— hydrogen, mono, bis or trihydroxylated $C_{1-4}$ alkyl
—$NH(CO—CH_2OCH_3)$ and
—$N(COCH_2OH)_2$.

Even more preferred, two of the $R^1$, $R^2$ and $R^3$ groups are equal and denote one or more moieties of the formulas
—$CONH—CH_2—CH_2—OH$
—$CONH—CH_2—CHOH—CH_2—OH$
—$CON(CH_3)CH_2—CHOH—CH_2OH$
—$CONH—CH—(CH_2—OH)_2$ and
—$CON—(CH_2—CH_2—OH)_2$, while the third group of $R^1$, $R^2$ and $R^3$ denotes
—$N(COCH_3)$—mono, bis or tris-hydroxy $C_{1-4}$ alkyl
—$N(COCH_2OH)$—hydrogen, $C_{1-4}$ alkyl, mono, bis or tris-hydroxy $C_{1-4}$ alkyl
$N(CO—CHOH—CH_3)$—hydrogen, mono, bis or trihydroxylated $C_{1-4}$ alkyl or
—$N(CO—CH—(CH_2OH)_2)$—hydrogen, mono, bis or tri-hydroxylated $C_{1-4}$ alkyl.

The process of the invention is particularly useful for the non-ionic dimeric compounds of formula (II)

$$R—N(R^7)—X—N(R^6)—R \qquad \text{Formula (II)}$$

or optical active isomers thereof,
wherein
X denotes a $C_3$ to $C_8$ straight or branched alkylene moiety optionally with one or two $CH_2$ moieties replaced by oxygen atoms, sulphur atoms or $NR^4$ groups and wherein the alkylene moiety optionally is substituted by up to six —$OR^4$ groups;
$R^4$ denotes a hydrogen atom or a $C_1$ to $C_4$ straight or branched alkyl group;
$R^6$ and $R^7$ denote a hydrogen atom or an acyl function; and each R independently is the same or different and denotes a triiodinated phenyl group, preferably a 2,4,6-triiodinated phenyl group, further substituted by two groups $R^5$ wherein each $R^5$ is the same or different and denotes a hydrogen atom or a non-ionic hydrophilic moiety, provided that at least one $R^5$ group in the compound of formula (II) is a hydrophilic moiety.

In formula (II) above, X preferably denotes a straight $C_3$ to $C_8$ alkylene chain optionally substituted by one to six —$OR^4$ groups. More preferably X denotes a straight $C_3$ to $C_5$ alkylene chain having at least one —$OR^4$ group, preferably at least one such group is in a position that is not vicinal to the bridge nitrogen atoms. More preferably the alkylene chain is substituted by one to three hydroxyl groups and still more preferably the alkylene chain is a straight propylene, butylene or pentylene chain substituted by one, two or three hydroxyl groups. Particularly preferred groups X are selected from 2-hydroxy propylene, 2,3-dihydroxy butylene, 2,4-dihydroxy pentylene and 2,3,4-trihydroxy pentylene, and most particularly X is the 2-hydroxy propylene entity. $R^4$ preferably denotes a hydrogen atom or a methyl group, most preferably a hydrogen atom.

The substituents $R^6$ and $R^7$ individually and preferably denote a hydrogen atom or a residue of an aliphatic organic acid, and in particular a $C_1$ to $C_5$ organic acid, such as an acyl group selected from formyl, acetyl, propionyl, butyryl, isobutyryl and valeriyl moieties. Hydroxylated and metoxylated acyl moieties are also feasible. In a particularly preferred embodiment the $R^6$ and $R^7$ groups in the compound of formula (II) denote hydrogen atoms, formyl moieties or acetyl moieties, most preferably formyl moieties.

Each of the iodinated R groups can be the same or different and preferably denote a 2,4,6-triiodinated phenyl group, further substituted by two groups $R^5$ in the remaining 3 and 5 positions in the phenyl moiety. The non-ionic hydrophilic moieties, $R^5$, may be any of the non-ionizing groups conventionally used to enhance water solubility. Hence, the $R^5$ substituents may be the same or different and shall preferably all denote a non-ionic hydrophilic moiety comprising esters, amides and amine moieties, optionally further substituted by a straight chain or branched chain $C_{1-10}$ alkyl groups, preferably $C_{1-5}$ alkyl groups, where the alkyl groups also may have one or more $CH_2$ or CH moieties replaced by oxygen or nitrogen atoms. The $R^5$ substituents may also further contain one or more groups selected from oxo, hydroxyl, amino or carboxyl derivative, and oxo substituted sulphur and phosphorus atoms. Each of the straight or branched alkyl groups preferably contains 1 to 6 hydroxy groups and more preferably 1 to 3 hydroxy groups. Therefore, in a further preferred aspect, the $R^5$ substituents are the same or different and are polyhydroxy $C_{1-5}$ alkyl, hydroxyalkoxyalkyl with 1 to 5 carbon atoms and hydroxypolyalkoxyalkyl with 1 to 5 carbon atoms, and are attached to the iodinated phenyl group via an amide or a carbamoyl linkage, preferably by amide linkages.

Particularly preferably, $R^5$ is selected from the group of:
—$CONH_2$
—$CONHCH_3$
—CONH—$CH_2$—$CH_2$—OH
—CONH—$CH_2$—$CH_2$—$OCH_3$
—CONH—$CH_2$—CHOH—$CH_2$—OH
—CONH—$CH_2$—$CHOCH_3$—$CH_2$—OH
—CONH—$CH_2$—CHOH—$CH_2$—$OCH_3$
—CON($CH_3$)$CH_2$—CHOH—$CH_2$OH
CONH—CH—($CH_2$—OH)$_2$
—CON—($CH_2$—$CH_2$—OH)$_2$
—CON—($CH_2$—CHOH—$CH_2$—OH)$_2$
—CONH—$OCH_3$
—CON($CH_2$—CHOH—$CH_2$—OH)($CH_2$—$CH_2$—OH)
—CONH—C($CH_2$—OH)$_2$ $CH_3$
—CONH—C($CH_2$—OH)$_3$
—CONH—CH($CH_2$—OH)(CHOH—$CH_2$—OH)
—NH($COCH_3$)
—N($COCH_3$) $C_{1-3}$ alkyl
—N($COCH_3$)-mono, bis or tris-hydroxy $C_{1-4}$ alkyl
—N($COCH_2OH$)—hydrogen, mono, bis or tris-hydroxy $C_{1-4}$ alkyl
—N(CO—CHOH—$CH_2OH$)—hydrogen, mono, bis or tri-hydroxylated $C_{1-4}$ alkyl
—N(CO—CHOH—CHOH—$CH_2OH$)—hydrogen, mono, bis or trihydroxylated $C_{1-4}$ alkyl
—N(CO—CH—($CH_2OH$)$_2$)—hydrogen, mono, bis or trihydroxylated $C_{1-4}$ alkyl and —N($COCH_2OH$)$_2$.

Even more preferably the $R^5$ groups will be equal or different and are selected from the group of —CONH—$CH_2$—$CH_2$—OH, —CONH—$CH_2$—CHOH—$CH_2$—OH, —CON($CH_3$)$CH_2$—CHOH—$CH_2OH$, —CONH—CH—($CH_2$—OH)$_2$ and —CON—($CH_2$—$CH_2$—OH)$_2$. Still more preferably both R groups are the same and the $R^5$ groups in each R are the same. In a particularly preferred embodiment, both R groups are the same, and preferably all $R^5$ groups denote the entity of formula —CONH—$CH_2$—CHOH—$CH_2$—OH.

Thus, preferred non-ionic dimeric compounds of the compositions prepared according to the invention include the compounds of formula (IIa-d):

Formula (II a-d)

| | |
|---|---|
| R—N(CHO)—X—N(CHO)—R | (IIa) |
| R—N(CHO)—X—N(CO(CH$_3$))—R | (IIb) |
| R—N(CHO)—X—NH—R | (IIc) |
| R—N(CO(CH$_3$))—X—N(CO(CH$_3$))—R | (IId) |

In formula (IIa-d), each group R has the meaning above, more preferably both iodophenyl groups R are the same and the $R^5$ groups all denote non-ionic hydrophilic moieties, and preferably the $R^5$ groups are linked to iodinated phenyl moiety by amide linkages. X preferably denotes straight chain alkylene groups with 3 to 5 carbon atoms and having one to three hydroxyl substituents at positions that are not adjacent to the nitrogen function.

Compounds of formula (IIa) are particularly preferred, in particular compounds having a monohydroxylated alkylene bridge X, in particular a monohydroxylated propylene bridge. Some preferred examples of contrast agents useful in the process of the invention include the compounds of formulas (III a) to (III u) provided in the application EP2010/050118, incorporated herein by reference. That application further provides a description of how to prepare the compounds (primary production) and the application with its description of a process for preparation is hereby incorporated by reference.

Most preferably the contrast agent used in the process of the invention is the compound of formula IIIa of application EP2010/050118, i.e. Compound I.

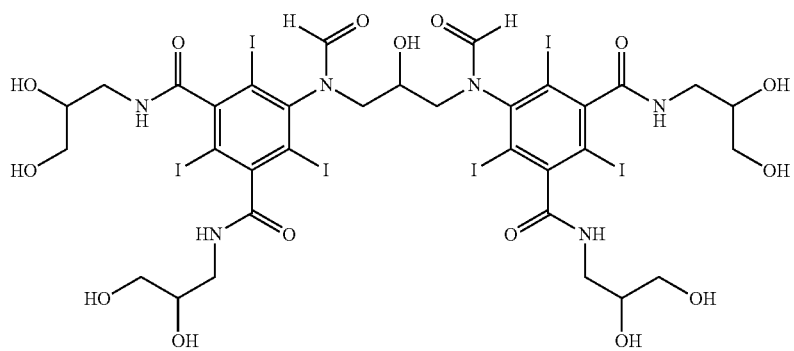

Formula (IIIa)-Compound I

Compound I can be prepared as outlined in WO 2009/008734. A general procedure is outlined on pages 16-20, and a specific method for preparation is provided in Example 1 of WO 2009/008734. The WO 2009/008734 application, with its description of a process for preparation is hereby incorporated by reference.

In another preferred embodiment the contrast agent used in the process of the invention is iodixanol.

The process of the invention is particularly useful for the secondary preparation of compositions comprising any X-ray contrast agents that require elevated temperature for dissolution and for X-ray compositions requiring low iodide levels.

The diagnostic composition prepared by the process of the invention preferably includes excipients and additives, such as salts. Any such excipients/additives may be added and included in the composition in any of the steps i) to iv) of the process of the invention. Adverse effects of non-ionic contrast media can be reduced by the inclusion of metal ions such as sodium and calcium ions in the diagnostic composition. Preferably, the diagnostic composition comprises a contrast agent as described above and a pharmaceutically acceptable carrier and dissolved therein a sodium compound and a calcium compound providing a sodium ion concentration of 10-100 mM, more preferably 30-80 mM and most preferably 35-60 mM, and a calcium ion concentration of 0.1-1.0 and preferably 0.1-0.7 mM.

For a preparation of a composition comprising a concentration of Compound I of 320 mg I/ml, the sodium ion concentration is preferably 42-47 mM, even more preferably 44-46 mM, and most preferably 45 mM. The calcium ion concentration for such composition is preferably 0.1-1.0 mM, more preferably 0.3-0.6 mM, even more preferably 0.4-0.5 mM and most preferably 0.5 mM.

The sodium compound and the calcium compound of the composition may be provided in the form of salts, i.e. the compounds include physiologically tolerable counter ions, e.g. selected from the group of chloride, sulphate, phosphate and hydrogen carbonate. Preferably, the sodium compound is sodium chloride and the calcium compound is calcium chloride.

The process of the invention hence preferably includes the addition of such salts to the diagnostic composition. The salts are added to the carrier and the contrast agent during any of the process steps. In a preferred embodiment these salts are added before or during step i) or before or during step iv).

The contrast agent is hence formulated with conventional carriers and excipients to produce a diagnostic composition. In addition to plasma ions, such as sodium and calcium ions, dissolved oxygen may be included. Further, chelating agents such as EDTA (ethylenediaminetetraacetic acid) or DTPA (diethylene triamine pentaacetic acid) may be included in the prepared composition to sequester metal ions from the solution. EDTA being preferred. Such additives may be added during any of the process steps, and are preferably added before or during step i) or iv).

In addition to the steps (i-iv) described, the process of the invention may further include the steps of:

Mixing the components, i.e. the carrier, the contrast agent and optional additives to completely dissolve the contrast agent in the carrier. Mixing means may be used and the mixing may be carried out by several mechanical mixing methods well known in the art, such as stirring in a mixing tank, using a static mixer or a mixing reactor. Such mixing is preferably carried out during step i) and step ii).

Filtration of the diagnostic composition, such as by micro- or ultrafiltration. Such filtration is optionally carried out after step ii). The filtration is performed to remove and reduce in quantity particles, particularly particles with a size above a certain limit, e.g. above 10 000 Daltons, and/or for removal of endotoxins, which have survived the heat treatment under reduced pH.

Dilution, i.e. diluting the composition to a concentration as desired. Such step is optionally carried out after step ii), iii) or iv).

Filling, capsling and labeling is optionally carried out after step iv).

Heat treatment after filling: It is very difficult to achieve a particle free atmosphere during the filling of the bottles. The bottles may also contain tiny particles, in spite of washing of the bottles. A final heat treatment, e.g. steam sterilization, of the filled and sealed bottles at a suitable temperature, above the saturation temperature of the contrast agent, is critical with respect of dissolving foreign particles brought to the bottles by dust and to deactivate the insoluble foreign particles present in the solution.

The pharmaceutically acceptable carrier is an aqueous solution, preferably pure water.

The diagnostic composition prepared by the process of the invention is in a ready to use concentration. Generally compositions in a ready to use form will have iodine concentrations of at least 100 mg I/ml, such as at least 150 mg I/ml, or with concentrations of at least 300 mg I/ml, e.g. 320 mg I/ml, or even 350, 360 or 400 mg I/ml.

The diagnostic composition prepared by the process of the invention is preferably for use in X-ray diagnosis. The composition may be administered as a bolus injection or by infusion. Further, the composition may be administered by intravascular, intravenous or intra-arterial administration. Alternatively, the composition may also be administered orally.

BRIEF DESCRIPTION OF THE DRAWINGS

FIG. 1: Iodide levels and end pH as a result of start pH and a heat load of 121° C. for 120 minutes, Compound I,320 mg I/ml.

FIG. 2: Iodide levels and end pH as a result of start pH and a heat load of 134° C. for 60 minutes, Compound I,320 mg I/ml.

FIG. 3: A possible production set up for the process of the invention, wherein:
I denotes Water for injection (WFI)
II denotes acid for pH adjustment
II denotes the X-ray contrast agent
IV denotes additives
A denotes a mixing tank
B denotes microfiltration/ultrafiltration
C denotes a holding tank
D denotes filling and capping
E denotes autoclaving
F denotes labelling and pack-off

EXAMPLES

Example 1

Stability of Compound I at Different pH

Experiments were performed to investigate the level of inorganic iodide generated as a result of degeneration of Compound I as a result of a pH and heating regime. Reference is made to FIGS. 1 and 2. The heat load was controlled by using a BIER-vessel for the steam heat sterilisation. Formulated Compound I (drug product, DP, 320 mg I/ml) was added 25% HCl to obtain 4 series of 6 vials with a pH of 2.0, 3.1, 4.0 and 7.7, respectively.

DP (10 ml) was filled in 10 ml vials. 3 vials from each series were autoclaved at 121° C. for 120 minutes and the remaining 3 vials were autoclaved at 134° C. for 60 minutes. The samples, including 2 reference samples, were subjected to pH and iodide analyses. The results from these studies showed that only a minor increase in iodide levels and no significant change in pH could be observed for the samples having a start pH in the range 2-4, while high iodide levels and a corresponding drop in pH was observed for the samples having a start pH of 7.7, as shown in FIGS. 1 and 2. Hence, this is a proof of concept for the process of the invention, reducing degeneration of the contrast agent when applying heat at reduced pH. These results enable a heating regime with sufficient heat load to ensure complete dissolution of any crystalline material in the bulk material, as an acceptable low level of free iodide.

Example 2

Possible Production Set Up for Secondary Production of Compound I

Reference is made to FIG. 3. Compound I is dissolved in water for injection (WFI) in the mixing tank (A). HCl is used to set the unbuffered solution to pH 3-3.5. Under these conditions, Compound I is stable enough to undergo heating well above the dissolution temperature (110-111° C./330 mg I/ml) for as long as it takes to achieve complete dissolution without causing the amount of free iodide to rise significantly (e.g. at 120-180° C. for 20-240 minutes). Subsequently, the heated solution of Compound I of e.g. 330-360 mg I/ml is cooled to 40-60° C. and diluted by a solution of TRIS/TRIS-HCl of a pH of approximately 8.0 to yield the final drug product formulation containing TRIS 10 mmol/l of pH 7.4-7.7 (measured at room temperature, 20-25° C.) and Compound I,320 mg I/ml.

This dilution and pH equilibration can be done either in the mixing tank or even as a rinsing step for a subsequent ultra filtration (B) if the filters tolerate low pH or alternatively in the ultrafiltrate after ultrafiltration.

If the process of the invention can be effective enough to ensure complete dissolution, ultrafiltration as a process step to remove undissolved crystals can possibly be omitted.

Example 3

Production Set Up Used for Secondary Production of 400 Litres of Compound I in a Concentration of 320 mg I/ml Reference is made to FIG. 3.

261 kg of Compound I was dissolved in 250 litres of water for injection (WFI) and added 44 g $Na_2Ca$-EDTA.$2H_2O$ in the mixing tank (A). HCl 5M was used to set the solution to pH 3. Under these conditions, to the composition underwent heating for 40 minutes at 122° C. Subsequently, the heated solution of Compound I of approximately 340 mg I/ml was cooled to approximately 80° C. and added the remaining excipients, being 29 g of $CaCl_2.2H_2O$, 1052 g of NaCl, 484 g of TRIS base and 346 ml of HCl 5M to yield a pH of 7.3. This solution was cooled to approximately 50° C. and filtered through a 10 kDa ultrafilter. The remaining WFI to yield a solution of 320 mg I/ml of compound I was used to rinse the ultrafilter by dilution of the concentrated retentate. The filtered solution was dispensed and autoclaved for 20 minutes at 121° C. After autoclaving, the concentration of inorganic iodide was 10 µg/ml, which is approximately a fifth of the concentration resulting from a conventional production not using the process of the invention.

The invention claimed is:

1. A process for the preparation of a composition comprising an X-ray contrast agent, comprising the steps of:
   i) adjusting the pH of a mixture comprising the X-ray contrast agent and a liquid carrier to within a range of 2.0 and less than 4.0, by adding an aqueous acid;
   ii) heating the pH-adjusted mixture of step i) to 60-200° C. for a sufficient time to form a completely dissolved solution of the X-ray contrast agent in the liquid carrier that has an iodine concentration of 270-400 mg I/mL;
   iii) cooling the solution of step ii) to 40-60° C.; and
   iv) adjusting the pH of the solution of step iii) to 7.0-8.0 using a buffer to form the composition, wherein the free iodide concentration in the X-ray composition is less than 25 µg I/mL, wherein the X-ray contrast agent is Iodixanol or Compound I:

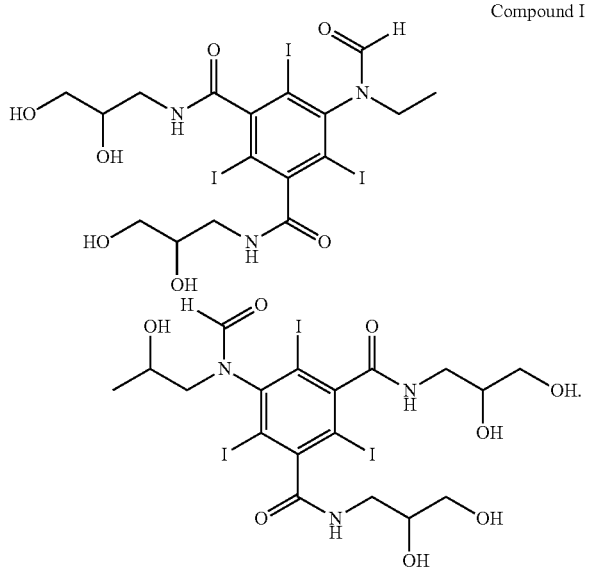

Compound I

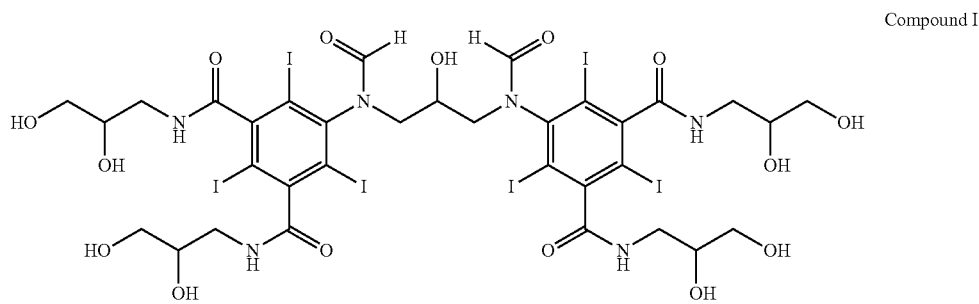 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound I

2. The process of claim 1, wherein the composition comprises an amount of free iodide below 20 μg I/ml.

3. The process of claim 1, wherein the pH adjustment in step i) is carried out by adding hydrochloric acid (HCl) to the mixture.

4. The process of claim 1, wherein the pH-adjusted mixture of step i) is heated for a period of 30-240 minutes in step ii).

5. The process of claim 1, wherein the pH is adjusted in step iv) by adding buffer couple TRIS/TRIS HCl to the solution.

6. The process of claim 1, wherein sodium and calcium ions are added in the form of salts during the process.

7. The process of claim 1, further comprising any of the optional steps of filtration, dilution, filling, capsling and labeling, and heat treatment after filling.

8. A process for the preparation of an X-ray composition comprising an X-ray contrast agent, wherein the X-ray contrast agent is compound I having a formula of and salts or optical active isomers thereof,
the method comprising the steps of
  i) adjusting the pH of a mixture comprising compound I and a liquid carrier to within a range of 2.0 and less than 4.0, by adding an aqueous acid;
  ii) heating the pH-adjusted mixture of step i) to 110-135° C. for 30-240 minutes to form a solution of compound I in the liquid carrier that has an iodine concentration of 320-380 mg I/mL;
  iii) cooling the solution of step ii) to 40-60° C.; and
  iv) adjusting the pH of the solution of step iii) to 7.0-8.0 using a buffer to form the X-ray composition,
  wherein the free iodide concentration in the X-ray composition is less than 20 μg I/mL.

9. The process of claim 8, wherein the pH adjustment in step i) is carried out by adding hydrochloric acid (HCl) to the mixture.

10. The process of claim 8, wherein the pH is adjusted in step iv) by adding buffer couple TRIS/TRIS HCl to the solution.

11. The process of claim 8, wherein sodium and calcium ions are added in the form of salts during the process.

12. The process of claim 8, further comprising any of the optional steps of filtration, dilution, filling, capsuling, and labeling, and heat treatment after filling.

13. The process of claim 8, further comprising performing a heat treatment step v) after step iv).

* * * * *